United States Patent [19]
Miller

[11] Patent Number: 5,741,230
[45] Date of Patent: Apr. 21, 1998

[54] HYPODERMIC NEEDLE EXTRACTION DISPOSAL SYSTEM AND DEVICE

[76] Inventor: Gary E. Miller, 16510 County Rd. 122, Mayer, Minn. 55360

[21] Appl. No.: 690,565

[22] Filed: Jul. 31, 1996

[51] Int. Cl.$^6$ ................................................. A61M 5/00
[52] U.S. Cl. .............................. 604/110; 604/187; 219/68
[58] Field of Search .................................... 604/110, 187; 219/68, 69; 206/365, 366; 422/21, 22

[56] References Cited

U.S. PATENT DOCUMENTS

| | | | |
|---|---|---|---|
| 4,628,169 | 12/1986 | Lung | 219/68 |
| 4,877,934 | 10/1989 | Spinello | 219/68 |
| 5,147,304 | 9/1992 | Fladung | 604/110 |
| 5,277,868 | 1/1994 | Langford | 422/21 |
| 5,288,964 | 2/1994 | Walker et al. | 219/68 |

Primary Examiner—John D. Yasko

[57] ABSTRACT

Disclosed herein is a syringe sterilization and disposal unit which utilizes a micro-processor controlled artificial intelligence for operation of the necessary functions to render a used syringe safe for disposal. The syringe sterilization unit includes an "opto-sensor" for signaling the positioning of the syringe for further clamping and processing operations. The lure of a syringe to be processed is exposed to heat from the heat heads to effect separation of the needle. The needle tip gripper jaw heads extract the syringe needle from the syringe body. The heat heads are further used to compress the lure of the syringe body to seal the syringe cavity. The extracted needle is then heated by a needle tip contactor for sterilization whereupon the needle and the sealed syringe cavity are then positioned into an appropriate bin for disposal and/or recycling.

17 Claims, 12 Drawing Sheets

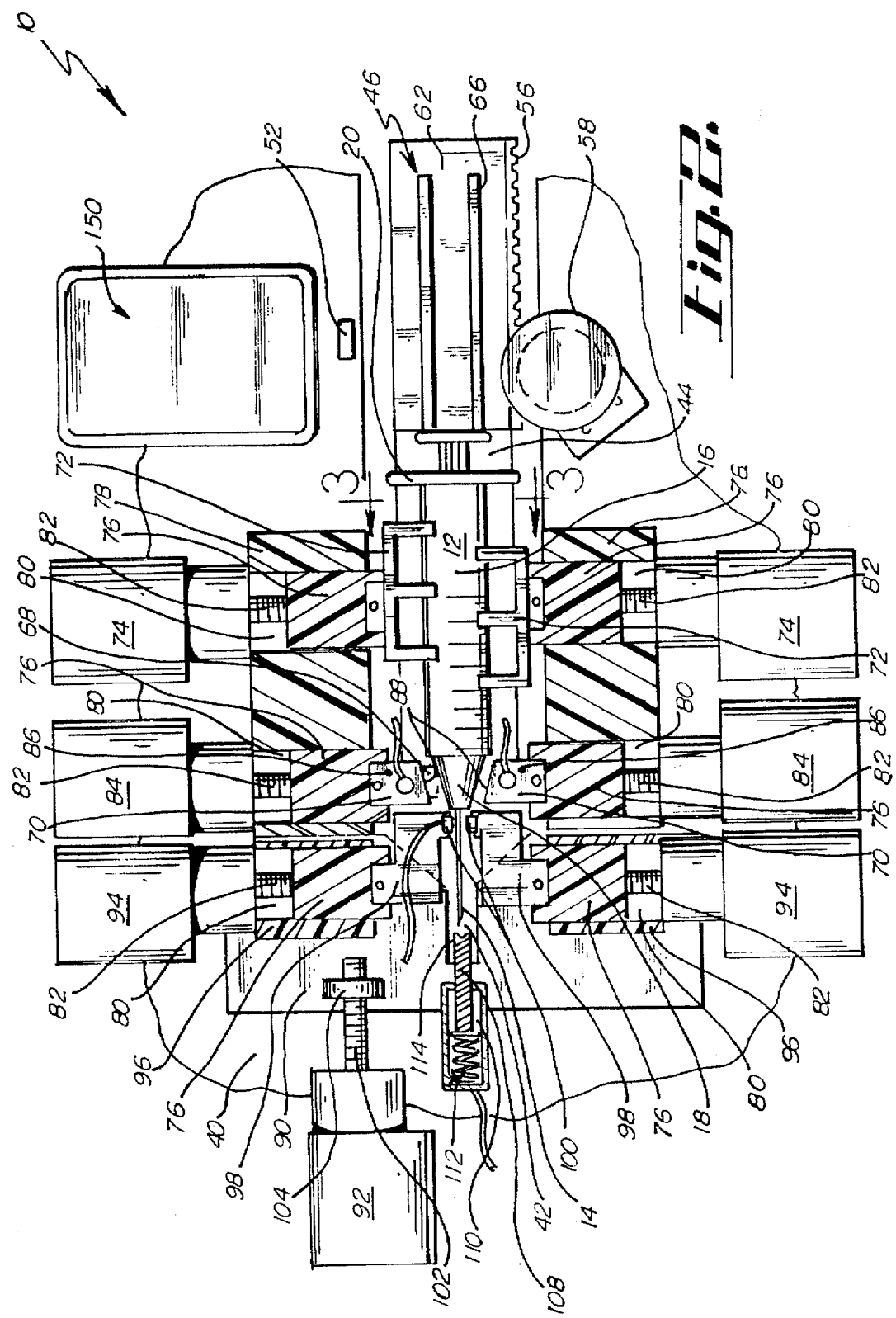

COMPONENT SIDE

SOLDER SIDE AS VIEWED THROUGH THE BOARD

HYPODERMIC NEEDLE EXTRACTION DISPOSAL SYSTEM AND DEVICE

BACKGROUND OF THE INVENTION

This invention relates generally to a hypodermic needle extraction disposal system and device which is preferably utilized to render used syringes safe for disposal and/or recycling.

The medical industry has experienced an exponential increase in the incidents of accidental needle punctures experienced during the disposal and/or storage of used syringes. Accidental needle punctures pose a potentially deadly and serious problem to medical care providers, as well as to individuals handling used syringes. Accidental "needle sticks" also may be costly to diagnose and/or treat. It is estimated that the expense to identify and treat a medical condition acquired as a result of a "needle stick" is within the range of between two thousand and five hundred thousand dollars ($2,000.00 and $500,000.00).

Medical industry insurers have been desperate to identify ways to eliminate and/or minimize the risk of inadvertent "needle sticks" to medical service providers and/or individuals involved in the handling and disposal of used syringes. In addition, self-insuring medical facilities are especially interested in a cost effective solution to eliminate the growing "needle stick" problem.

Currently, used syringes are collected and/or held in a heavy walled bag known in the industry as a sharp bag or box. Currently, a care giver is required to deposit a used syringe and needle into an appropriate sharp bag or box. A number of disadvantages arise through the use of a sharp bag or box by a care giver. Initially, a care giver is required to exercise extreme caution to not acquire an inadvertent "needle stick" during the placement of a used syringe into a sharp bag. In addition, used needles protruding from a sharp bag pose a serious risk to a care giver as the sharp bag becomes filled to capacity. Persons handling a sharp bag filled with used needles also must be extremely careful to not obtain an accidental "needle stick", especially when emptying the syringes or transporting the sharp bag. In addition, frequently sharp bags or boxes are not automatically sealed, protecting individuals from inadvertent "needle sticks" and used syringes are not sterilized prior to transportation, storage, and/or disposal.

Additional risks are also present with respect to the handling of used syringes outside of a medical facility environment. Home health care, such as with individuals having diabetes, may be required to dispose of a number of used syringes each day. Additionally, used syringes may be disposed of without destruction, which, in turn, may further expose the public to the danger of improper reuse.

The considerations referenced-above are just a few of the major problems associated with the handling and disposal of used syringes. The considerations identified-above also show a critical need for a device which safely and effectively renders used syringes harmless and non-reusable for disposal and/or recycling.

The following described hypodermic needle extraction disposal device and system safely and effectively renders a used syringe safe for disposal and recycling and minimizes the risk of inadvertent "needle sticks" and/or improper reuse of dangerous syringes.

SUMMARY

Disclosed herein is a syringe sterilization and disposal unit which utilizes a micro-processor controlled artificial intelligence for operation of the necessary functions to render a used syringe safe for disposal. The syringe sterilization unit includes an "opto-sensor" for signaling the positioning of the syringe for further clamping and processing operations. The lure of syringe to be processed is exposed to heat from the heat heads to effect separation of the needle. The needle tip gripper jaw heads extract the syringe needle from the syringe body. The heat heads are further used to compress the lure of the syringe body to seal the syringe cavity. The extracted needle is then heated by a needle tip contactor for sterilization whereupon the needle and the sealed syringe cavity are then positioned into an appropriate bin for disposal and/or recycling.

It is a principle object of the present invention to provide a new and improved hypodermic needle extraction/disposal system and device of relatively simple and inexpensive design, construction, and operation which fulfills the intended purpose of rendering safe a used syringe without fear of injury to persons and/or damage to property.

It is another principle object of the present invention to sterilize and separate the needle and syringe body from a used syringe for safe disposal and recycling.

It is still another principle object of the present invention to provide a fully automated methodology for processing used syringe and needle units for safe and effective handling in a medical, home, or office environment.

It is still another principle object of the present invention to provide a fully automated methodology for processing a used syringe and needle unit through the use of artificial intelligence.

It is still another principle object of the present invention to provide a hypodermic needle extraction disposal device which is flexible and which may be used with any size of syringe body and/or needle without adjustment, alignment, and/or calibration of the components of the device.

It is still another principle object of the present invention to provide a hypodermic needle extraction disposal device which includes interchangeable components for the facilitation of maintenance and construction of the device as well as the promotion of cost efficiency.

It is still another principle object of the present invention to provide a hypodermic needle extraction disposal device which requires no special training or operation skills for the processing and sterilization of used syringes.

It is still another principle object of the present invention to provide a hypodermic needle extraction disposal device which is adapted to process used syringes in single quantities or in multiple repetitive quantities as desired by an individual.

It is still another principle object of the present invention to sterilize a used syringe needle and blunt the tip, rendering a used syringe needle safe to medical providers and persons handling a used syringe for disposal.

It is still another principle object of the present invention to seal the body of a used syringe having the needle extracted rendering the used syringe body safe to medical providers and persons handling a used syringe body for disposal.

Still another principle object of the present invention is to provide a space efficient hypodermic needle extraction disposal device which may be easily adapted for bedside use, on a moveable cart, in a patient's home, or in an emergency vehicle.

Still another principle object of the present invention is to provide a hypodermic needle extraction disposal device providing absolute orientation of various component assemblies maintaining vertical, horizontal, and rotational integrity of the features of the device.

A feature of the present invention includes a housing or enclosure having an LED indicator or signaling device for communication of the ready status or operation of the hypodermic needle extraction disposal device.

Another feature of the present invention is a housing/enclosure having a needle bin and a syringe bin for storage of sterilized needles and syringe bodies following processing and prior to disposal and/or recycling.

Still another feature of the present invention is a means for access which may include a syringe receiving door which may be used for regulating access of used syringes into the hypodermic needle extraction disposal device for processing.

Still another feature of the present invention is a syringe receiving door opto-sensor which may be used to electrically signal the syringe receiving door for opening to permit access of a used syringe into the hypodermic needle extraction disposal device for processing.

Still another feature of the present invention is a transfer carriage assembly which may include a transfer carriage and transfer carriage motor which is used to introduce a used syringe into a desired location for initiation of sterilization processing procedures.

Still another feature of the present invention is a transfer carriage opto-sensor which is electrically in communication with the micro-processor for signaling the presence of a used syringe for sterilization processing procedures.

Still another feature of the present invention is a transfer carriage stop opto-sensor which is electrically in communication with the micro-processor for signaling the presence of a used syringe proximate to the barrel clamp assembly for further sterilization processing procedures.

Still another feature of the present invention is a barrel clamp assembly which may include oppositely disposed barrel clamp heads and barrel clamp motors which may be utilized to position any size of syringe and particularly a syringed needle into a specific position within a desired x-y plane for sterilization and processing.

Still another feature of the present invention is a cartridge heater assembly which may include oppositely disposed ferrule clamp motors and cartridge heaters having heat heads which may be utilized for heating and softening of the lure of a syringe body permitting separation of a needle from the lure.

Still another feature of the present invention is a needle extraction assembly which may include a needle extraction platform and needle extraction platform motor for positioning of needle tip gripper jaws proximate to the needle of a syringe to be sterilized and processed.

Still another feature of the present invention includes a pair of oppositely disposed needle tip clamp motors which manipulate the needle tip gripper jaws into contact with a syringe needle during sterilization and processing procedures.

Still another feature of the present invention includes a needle tip contactor assembly having an inverted v-shape which is adapted for contact to, and heating of, a syringe needle for sterilization and disposal procedures.

Still another feature of the present invention includes an electric control system having a power supply, a microprocessor, a memory, a plurality of sensing sequences, a needle sensing section, a motor controller section, and a heater controller section for controlling the sterilization and processing sequences to be implemented upon a used syringe through an event-based control system, as opposed to a timing sequence control system, where the electronic control system senses various voltage drops or thresholds for the termination and/or initiation of sterilization, transportation, and disposal procedures which render a used syringe safe for handling by medical providers or others.

BRIEF DESCRIPTION OF THE DRAWINGS

FIG. 2 is a cross-sectional top view of the hypodermic needle extraction disposal device taken along the line of 2—2 of FIG. 1;

Figure 1:
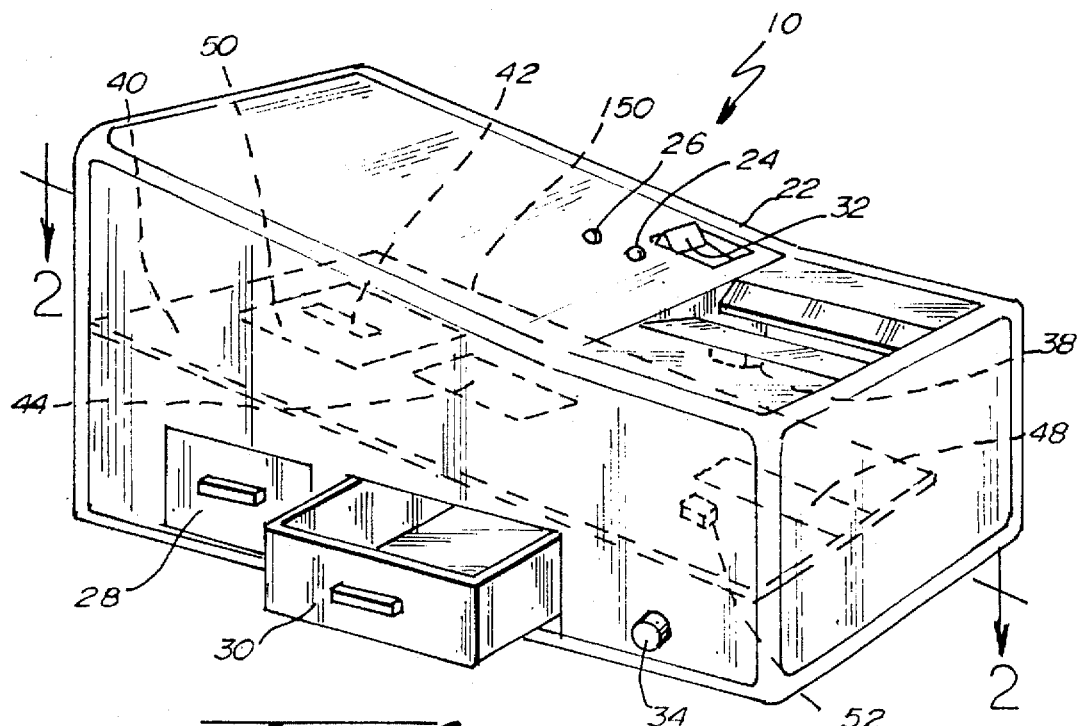
FIG. 1 is an isometric view of the housing of the hypodermic needle extraction disposal device.

This application is derived from a co-pending provisional patent application, Ser. No. 60/001,745, filed on Aug. 1, 1995, for a HYPODERMIC EXTRACTION/DISPOSAL SYSTEM AND DEVICE where the invention disclosed within this application has been invented by the same inventor as the co-pending provisional patent application, Ser. No. 70/001,745, referenced above.

SPECIFICATION OF THE PREFERRED EMBODIMENT

The purpose of this invention is to provide an effective and safe hypodermic needle extraction and disposal device for processing of a used hypodermic needle assembly for separation of the needle from the body of the syringe, sterilizing the needle, sealing the syringe body cavity, and safely disposing of the needle and syringe body following processing.

One form of the invention is illustrated and described herein. The hypodermic needle extraction disposal system and device is indicated in general by the numeral 10.

The hypodermic needle extraction and disposal device 10 is generally used for processing and sterilization of a syringe 12 which generally includes a needle 14, a body 16, a lure 18, and a plunger 20. A wide variety of syringe sizes, shapes, and lengths may be available for use within the medical industry. Syringes 12 may vary in size from a body 16 having an approximate diameter dimension of three eights of an inch for insulin delivery, to a body 16 having a diameter dimension approximating three quarters of an inch for a blood draw syringe 12. It should be noted that even larger syringes may be processed, sterilized, and rendered safe by the hypodermic needle extraction and disposal device 10 at the discretion of an individual. It should also be noted that the lure 18 of a syringe 12 is generally of a standard size and configuration. It should further be noted that the hypodermic needle extraction disposal device 10 may be used on a variety of syringes 12 having needles 14 varying in diameter dimensions from a twenty-eight gauge thickness to a fourteen gauge thickness.

The hypodermic needle extraction and disposal device 10 is generally enclosed within a housing 22. The housing 22 is generally formed of a lightweight, yet sturdy plastic material as preferred by an individual. It should be noted, however, that any material may comprise the housing 22 at the discretion of an individual provided that the essential functions, features, and attributes described herein are not sacrificed.

The housing 22 preferably is of a compact size in order to facilitate use within a home environment such as on a night stand, a medical office environment such as on a shelf, a medical facility environment such as for use on a cart, or facilitates a compact size for utilization within an ambulance or other emergency-type of vehicle. It should be noted that the housing 22 may also include a handle to facilitate the transportation and/or storage of the hypodermic needle extraction and disposal device 10.

The exterior of the housing 22 may contain a ready indicator lamp or LED 24 which may be utilized to signal to an operator the availability of the hypodermic needle extraction and disposal device 10 for use in processing and sterilization of a used syringe 12. The exterior of the housing 22 may also include a bin full indicator lamp or LED 26 which may be utilized to signal to an operator the necessity for replacement of either the needle bin 28 and/or the syringe body bin 30. The bin full indicator lamp 26 signals an operator of a condition where either the needle bin 28 or the syringe body bin 30 have become filled following the processing of a plurality of used syringes 12.

The exterior of the housing 22 may also include a power switch 32 for engaging the hypodermic needle extraction and disposal device 10. The exterior of the housing 22 may also include a power input jack 34 which may be utilized to supply power to the hypodermic needle extraction and disposal device 10. The power input jack 34 may be utilized as a self-contained battery recharging system which may be powered by either a wall mounted transformer in an institutional/home environment or may be charged/recharged by a mobile twelve volt source such as a cigarette lighter of a vehicle.

The exterior of the housing 22 may also include a syringe guide cutout which is preferably used for orientating a syringe 12 into a proper position for introduction into the hypodermic needle extraction and disposal device 10. The syringe guide cutout preferably enhances the safety of the hypodermic needle extraction and disposal device 10 by providing a self-contained area for a syringe 12 prior to processing which prevents an operator or medical service provider from receipt of an accidental "needle stick". The syringe guide cutout is preferably proximate to a syringe receiving door 36 which provides access into the hypodermic needle extraction and disposal device 10.

The syringe guide cutout may also be integral to a hopper mechanism (not shown) which may be utilized to store a number of used syringes 12 for automatic processing by the hypodermic needle extraction and disposal device 10. The hopper mechanism may function on the same principles as a clip for ammunition, a gravity drop via a channel, a standard v-shaped hopper, or a conveyor, as desired by an individual. It should be noted that any type of hopper may be utilized by an individual, and that the options discussed herein are provided for illustrative purposes only and have not been provided as limitations with respect to the forms for which the hopper may be embodied.

The syringe receiving door 36 is preferably operated by a solenoid actuation means which is electrically controlled by the electronic control system 150. In general, the syringe receiving door 36 is opened via the solenoid actuation means for permitting a used syringe 12 to drop into the hypodermic needle extraction and disposal device 10 for processing.

The syringe receiving door 36 may be of a type which includes a cantilever mechanism, has a platform which is retracted or slid laterally for the provision of the vertical drop of a syringe into the hypodermic needle extraction and disposal device 10; or is a platform which includes a hinge permitting the platform to drop into the interior of the housing 22 at the preference of an individual. In the preferred embodiment, the syringe receiving door 36 is of a type which slides laterally or is mounted on a hinge which may drop into the interior of the housing 22 for permitting access of the used syringe 12 into the hypodermic needle extraction and disposal device 10.

In both of these embodiments, a first angled ramp is positioned below the syringe receiving door 36 to initially engage the falling syringe 12. A second ramp is then positioned approximately one inch below the first ramp and is further positioned at an angle of approximately 90° with respect to the first ramp. The positioning of the first and second ramps facilitates the alignment of a syringe 12 into a desired orientation for engagement to a transfer carriage 46. It should be noted that if the syringe 12, as proceeding down the first ramp, is not horizontally level, then the second ramp functions to horizontally align the syringe 12 for further engagement to the transfer carriage 46.

A receiving door opto-sensor 38 is preferably adjacent to the syringe receiving door 36. The receiving door opto-sensor 38 functions to sense the presence of a syringe 12 being placed proximate to the syringe receiving door 36 and, if no other processing functions are occurring within the hypodermic needle extraction and disposal device 10, the receiving door opto-sensor 38 will electrically signal the electronic control system 150 to initiate the release of the solenoid controlled syringe receiving door 36, permitting a syringe 12 to drop into the transfer carriage 46 to initiate processing operations. The syringe receiving door 36 will then return to its original position. The receiving door opto-sensor 38 is a proximity device which may detect the presence of a non-conductive material within a certain distance. The receiving door opto-sensor 38 does not physically make contact with a syringe 12, however, the receiving door opto-sensor 38 may optically sense the presence of the syringe 12 proximate to the syringe receiving door 36 for the initiation of processing procedures.

The communication by the receiving door opto-sensor to the electronic control system 150 of the presence of a syringe 12 proximate to the syringe receiving door 36, results in the opening of the syringe receiving door 36 only at such time as the hypodermic needle extraction and disposal device 10 has completed processing of a previous syringe 12 and is ready to initiate further processing procedures.

The interior of the housing 22 preferably includes a power supply 39 which is preferably electrically connected to the electronic control system 150. The power supply 39 may be a rechargeable twelve volt battery 116 or any other preferred power supply 39 as desired by an individual.

The interior of the housing 22 may also include an inclined base platform 40. The base platform 40 is inclined with respect to the housing 22 to facilitate the retention of biological or other substances within the interior of the body 16 of the syringe 12 following extraction of the needle 14. It should be noted that the processing procedures for the syringe 12 occur such that the needle 14 is always retained at a higher elevation than the body 16 of the syringe 12. The elevation of the needle 14 with respect to the syringe body 16 facilitates in the retention of biological or other substances within the body 16 by the minimization of gravity affects, thereby eliminating the dripping of substances from the internal syringe cavity.

The inclined base platform 40 also includes a needle aperture 42 and a syringe body aperture 44. The needle aperture 42 and the syringe body aperture 44 enable a processed needle 14 and/or a processed syringe body 16 to fall through the inclined base platform 40 for storage in the respective needle bin 28 or syringe body bin 30 prior to disposal and/or recycling.

It should be noted that the needle bin 28 and/or the syringe body bin 30 may be readily replaced and disposed of as filling occurs.

The inclined base platform 40 also includes a transfer carriage channel 48 which is preferably adapted for receiving engagement of the transfer carriage 46 establishing a linear range of motion for the transfer carriage 46 within the hypodermic needle extraction and disposal device 10.

The inclined base platform 40 also includes a needle extraction assembly channel 50 which is preferably adapted for sliding and receiving engagement of the needle extraction assembly during processing of a used syringe 12. The needle extraction assembly channel 50 preferably provides a range of linear motion for the needle extraction assembly during use of the hypodermic needle extraction and disposal device 10.

A transfer carriage assembly generally transports a used syringe 12, as received from the syringe receiving door 36, for processing by the barrel clamp assembly. In general, the transfer carriage assembly is formed of a means for stopping which may include the transfer carriage opto-sensor 52, a transfer carriage 46 having a transfer carriage gear rack 56, and a transfer carriage motor 58 having a gear 60.

The transfer carriage 46, when positioned in the at rest location, is generally below the syringe receiving door 36. The transfer carriage 46 is generally formed of a transfer carriage base 62 which includes an alignment member 64 which is adapted for engagement within the transfer carriage channel 48 of the inclined base platform 40. The transfer carriage 46 is adapted for linear forward and rearward movement of approximately five inches within the transfer carriage channel 48.

It should be noted that the alignment member 64 may be integral to the transfer carriage base 62 or may be affixed thereto at the discretion of an individual.

Figure 4:
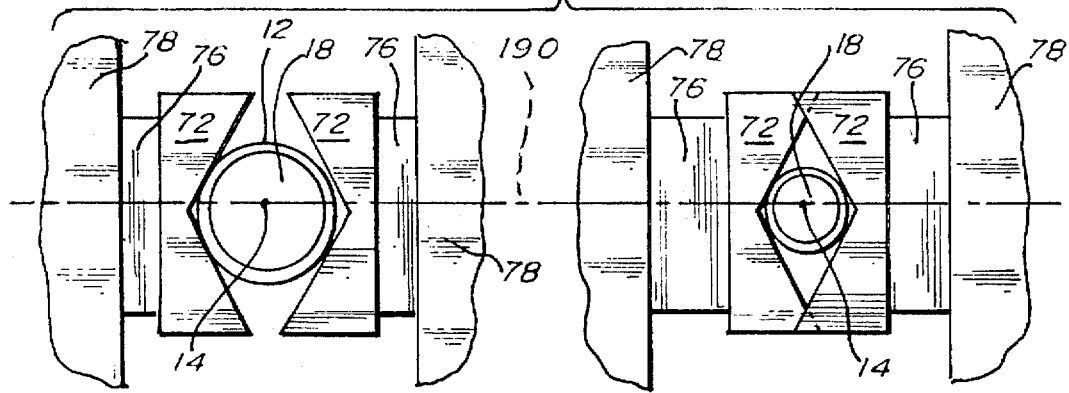
FIG. 4 is a detailed cross-sectional end view of the barrel clamp heads taken along the line of 3—3 of FIG. 2, showing centerline 190.

The transfer carriage 46 may include a pair of upwardly and outwardly diverging alignment arms 66 which assist in positioning of a syringe 12 centrally within the transfer carriage 46. It should be noted that the alignment arms 66 do not extend upwardly above a center line 190 for the syringe 12. (FIG. 4)

The transfer carriage 46 is preferably moved forwardly and rearwardly by the engagement of the transfer carriage motor 58 which, in turn, rotates the gear 60 which is engaged to the transfer carriage gear rack 56. The engagement of the transfer carriage motor 58 occurs through the receipt of signals from the electronic control system 150.

A transfer carriage opto-sensor 52 is preferably positioned adjacent to the transfer carriage 46 when the transfer carriage 46 is positioned in the at-rest location being aligned with the syringe receiving door 36. The transfer carriage opto-sensor 52 will identify the presence of a syringe 12 on the transfer carriage 46 which will signal the electronic control system 150 to initiate sterilization and processing procedures. The electronic control system 150 then signals the transfer carriage motor 58 to rotate in a counter clockwise direction engaging the gear 60 as connected to the transfer carriage gear rack 56 to forwardly position the transfer carriage 46 and syringe 12 proximate to the barrel clamp assembly. It should be noted that if the presence of a syringe 12 on the transfer carriage 46 is not identified by the transfer carriage opto-sensor 52, then a signal will be generated to the electronic control system, necessitating the return of the transfer carriage 46 to the at rest position, which is adjacent to and below the syringe receiving door 36.

The forward motion of the transfer carriage 46 is limited by the means for stopping which may be formed of a transfer carriage stop opto-sensor 68 which is positioned adjacent to the forward or leading edge of the barrel clamp assembly. The means for stopping or transfer carriage stop opto-sensor 68 is preferably adapted for sensing and signaling the presence of the lure 18 of the syringe 12 in a desired forward location.

The transfer carriage stop opto-sensor 68 initiates a signal to the electronic control system 150 upon sensing of the forward or leading edge of the lure 18 of the syringe 12. The transfer carriage stop opto-sensor 68 enables the processing of syringes 12 having varying lengths by terminating the forward motion of all syringes 12 at a precise forward position. At this position, the lure 18 is presented in an exact proximity to the heat heads 70 of the barrel clamp assembly.

The transfer carriage stop opto-sensor 68 is also a proximity device which may detect the presence of a non-conductive material within a certain distance, such as a syringe 12.

Upon the retrieval of the syringe 12 from the transfer carriage 46 by the barrel clamp assembly, the transfer carriage stop opto-sensor 68 signals the electronic control system 150 whereon retraction of the transfer carriage 46 to an original at-rest position adjacent to the syringe receiving door 36 occurs. It should be noted that the transfer carriage stop opto-sensor 68 does not require recalibration dependent upon the size of the syringe 12 to be processed because the lures 18 of the syringe 12 are generally mass produced of the same dimensions where the only variance occurs with respect to the needle diameter which may vary in size from a 26 gauge thickness to an 18 gauge thickness.

It should also be noted that the means for stopping may be formed of other alternatives as desired by an individual, including, but not limited to, the use of the forward or leading edge of the transfer carriage channel 48 to function as a limit for the forward movement of the transfer carriage 46. Alternatively, a tab, ledge, or wall may be affixed or integral to the inclined base platform 40, or to the barrel clamp assembly to limit the forward movement of the transfer carriage 46 at the discretion of an individual. In the preferred embodiment, the transfer carriage stop opto-sensor 68 is used as the means for stopping in order to provide maximum flexibility with respect to the sensing of varying sized syringes 12 to be sterilized and processed by the hypodermic needle extraction and disposal device 10.

The return of the transfer carriage 46 to the start position enables the transfer carriage 46 to be ready to receive another syringe 12 for sterilization and processing.

The transfer carriage stop opto-sensor 68 communicates a signal to the electronic control system 150 for initiation of processing procedures by the barrel clamp assembly upon the detection of the lure 18.

The barrel clamp assembly is generally utilized to raise the syringe 12 off the transfer carriage 46 and to securely clamp the syringe body 16 during sterilization procedures. The barrel clamp assembly preferably utilizes a self-centering pair of oppositely disposed barrel clamp heads 72 for centering 190 of the needle 14 in a desired x-y coordinate regardless of the varying diameters of the syringe bodies 16. (FIG. 4)

In general, the barrel clamp assembly is formed of a pair of oppositely disposed barrel clamp motors 74, each barrel clamp motor 74 having a barrel clamp head 72, and a square plunger 76. The square plungers 76 are preferably slidably engaged to motor mount blocks 78 which may be affixed or integral to the inclined base platform 40 as preferred by an individual.

The motor mount blocks 78 are preferably rectangular in shape, having square plunger channels 80 which are adapted for the sliding receipt of the square plungers 76. The motor mount blocks 78, having the square plunger channels 80, facilitate the ease of manufacture and/or maintenance for the hypodermic needle extraction and disposal device 10.

The barrel clamp motors 74 are engaged to the square plungers 76 via screw shafts 82 which, in turn, are engaged to nut certs (not shown) which are integral to the interior of the square plungers 76. A barrel clamp head 72 is engaged to each square plunger 76 extending inwardly therefrom adapted for engagement to the syringe body 16 during the sterilization and processing procedures of the syringe 12.

The pair of barrel clamp motors 74 preferably move the square plungers 76 having the barrel clamp heads 72 inwardly for engagement to the syringe 12 during the use of the hypodermic needle extraction disposal device 10. The pair of barrel clamp heads 72 are preferably formed in an opposing V-shaped configuration which facilitates the application of an identical clamping pressure to be implemented to the body 16 of a syringe 12 regardless of the diameter of the body 16. The current or voltage required for clamping of the syringe body 16 by the barrel clamp motors 74 may then be sensed and/or analyzed by the electronic control system 150 which, upon sensing of a pre-established voltage or current threshold, signals the barrel clamp motors 74 to hold the barrel clamp heads 72 in a desired position.

The opposing V-shaped clamps of the barrel clamp heads 72 preferably engage a syringe body 16 below the center line in order to facilitate the elevation and lifting of the syringe 12 for centering 190 in a desired x and y coordinate. (FIG. 4) The opposing V-shaped clamps of the barrel clamp heads 72 obtain an identical x and y coordinate for the needle 14 regardless of the size of the needle 14, or the diameter dimension for the body 16 of the syringe 12.

The utilization of the square plungers 76 within the square plunger channels 80, as held within the motor mount blocks 78, provide for absolute orientation of the barrel clamp heads 72 maintaining vertical, horizontal, and rotational integrity during operation of the hypodermic needle extraction and disposal device 10. Utilization of the square plungers 76 eliminate the possibility of rotation of the barrel clamp heads 72 out of position during use of the hypodermic needle extraction and disposal device 10. The desired x and y coordinate for positioning the needle 14 is thereby assured. (FIG. 4) In addition, no moving parts are used as components for the square plungers 76. Therefore, the elements for the barrel clamp assembly are not susceptible to wear.

The square plungers 76 include a recessed adapted front surface which permits an individual to substitute or interchange various heads such as the heat heads 70 of the cartridge heater assembly for the barrel clamp heads 72. The recessed adapter front surface thereby permits the interchange between the components of the hypodermic needle extraction and disposal device 10 thereby facilitating ease of manufacture, assembly, and maintenance.

The utilization of square plungers 76 provide a constant resistance or friction for the respective motors in either the inward or outward direction, facilitating the recognition by the electronic control system 150 of the power requirements for comparison to predetermined thresholds which, in turn, are utilized for rendering decisions by the microprocessor 118. The contact of the barrel clamp heads 72 with the syringe 12 thereby enables the electronic control system 150 to sense a variation in the voltage or current requirements for the barrel clamp motors 74. This variation in voltage or current requirements enables the electronic control system 150 to function as an event-based system as opposed to a timing sequence. In addition, the utilization of the square plungers 76 within the motor mount blocks 78 reduce the susceptibility of the barrel clamp assembly to contamination of dirt or interference with any other part of the hypodermic needle extraction disposal device and further limit the travel of the square plungers 76, reducing wear and extending the useful life of the barrel clamp assembly. In the preferred embodiment, the square plungers 76 travel inwardly and outwardly at a very small distance of approximately no more than one quarter to one half inch, thus minimizing wear for the barrel clamp assembly.

The transfer carriage stop opto-sensor 68 preferably signals the electronic control system 150 to initiate the grasping of a syringe 12 from the transfer carriage 46. The electronic control system 150 then signals the barrel clamp motors 74 to inwardly move the square plungers 76 and barrel clamp heads 72 inwardly for engagement to the body 16 of the syringe 12. The engagement between the barrel clamp heads 72 and the syringe body 16 elevates the syringe body 16, positioning the needle 14 in a desired x and y coordinate. (FIG. 4) As the inward positioning of the square plungers 76 and barrel clamp heads 72 continues and increased pressure is exerted upon the body 16. The barrel clamp motors 74 will then signal the electronic control system 150 of a necessity for more power. Once a certain power demand threshold has been encountered, the electronic control system 150 will signal the barrel clamp motors 74 to hold in a desired position during the remainder of the sterilization and processing procedures of a used syringe 12.

It should be noted that the barrel clamp heads 72 are required to engage the body 16 of a syringe 12 below a center line 190. Therefore, the engagement of the barrel clamp heads 72 to a syringe 12, proximate to a transfer carriage 46, requires that the alignment arms 66 not extend upwardly to a position proximate to the centerline 190 of a syringe 12 having a small diameter approximating three eighths inch as used for the treatment of diabetes. Therefore, the barrel clamp heads 72 may preferably engage a small diameter syringed body 16 below centerline 190 for elevation into the desired x-y coordinate. (FIG. 4)

The request by the barrel clamp motors 74 for additional current and/or voltage communicates to the electronic control system 150 that the needle 14 has been positioned in a desired x-y coordinate whereon the electronic control system 150 signals the cartridge heater assembly to move inwardly to engage the lure 18 of the syringe 12. In general, the cartridge heater assembly is formed of a pair of ferrule clamp motors 84, square plungers 76 positioned within square plunger channels 80, aluminum heat heads 70, thermal couples 86, and cartridge heaters 54.

It should be noted that the advantages as described for the square plungers 76, motor mount blocks 78, and square plunger channels 80 as described for the barrel clamp assembly are equally applicable to the cartridge heater assembly described herein. It should also be noted that the square plungers 76, motor mount blocks 78, and square plunger channels 80 function identically between the cartridge heater assembly and the barrel clamp assembly as earlier described.

The ferrule clamp motors 84 preferably engage the square plungers 76 through the utilization of screw shafts 82 and cert nuts as earlier described. The recessed adapted front surface of the square plungers 76 provide flexibility for accommodation of heat heads 70.

Upon the positioning of the needle 14 in a desired x-y coordinate, (FIG. 4) the electronic control system 150 signals the ferrule clamp motors 84 to inwardly position the square plungers 76 having the heat heads 70 into contact with the lure 18 of the syringe 12.

Figure 5:
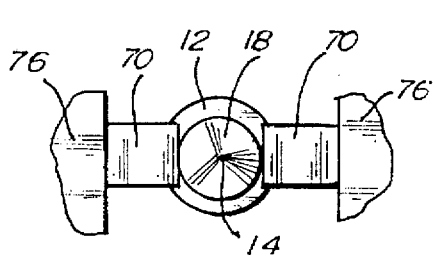
FIG. 5 is a front detailed view of the cartridge heaters.

The electronic control system 150 initiated the application of power to the cartridge heaters 54 and heat heads 70 as regulated by thermal couples 86 when the transfer carriage opto-sensor 52 signaled the electronic control system 150 of the presence of a syringe 12 on the transfer carriage 46. As such, the heat heads 70 have already obtained a temperature of between 400° and 500° fahrenheit when the ferrule clamp motors 84 receive a signal to position the heat heads 70 into contact with the lure 18 of the syringe 12. The ferrule clamp motors 84 will inwardly position the heat heads 70 until such time as an increase in the current/voltage is requested, indicating contact with the lure 18. (FIG. 5) The electronic control system 150 will then signal the ferrule clamp motors 84 to terminate the inward positioning of the heat heads 70 continuing engagement of the heat heads 70 with the lure 18 of the syringe 12. The heat heads 70 then are utilized to soften the lure 18 to facilitate the extraction of the needle 14 from the syringe 12 by the needle extraction assembly.

It should be noted that the heat heads 70 include an angular contact surface 88 which is adapted to flushly engage the lure 18 of the syringe 12 over the entire length of the respective heat head 70.

It should also be noted that when the heat heads 70 have acquired a temperature of approximately 400° fahrenheit, that the thermalcouples 86 will signal the electronic control system 150 to terminate/regulate power for the provision of further heat to the heat heads 70. An additional temperature increase to the heat heads 70 is not desired in order to reduce the risk that the heat heads 70 will melt the plastic lure 18 of the syringe 12. It is an object of the heat heads 70 to soften the lure 18 for extraction of the needle 14, however, it is not an object of the heat heads 70 to melt the lure 18. In addition, it should be noted that sufficient power is provided as regulated by the thermalcouples 86 to retain the heat head 70 at a temperature of approximately 400° during the softening of the lure 18.

Simultaneously to the engagement of the cartridge heater assembly for heating of the lure 18, the electronic control system 150 signals the implementation of the needle extraction assembly for grasping the needle 14.

In general, the needle extraction assembly is formed of a needle extraction platform 90, a needle extraction motor 92, a pair of needle tip clamp motors 94, needle extraction motor mount blocks 96, square plungers 76, square plunger channels 80, and a pair of needle tip gripper jaws 98, each having carbide grippers 100.

Figure 3:
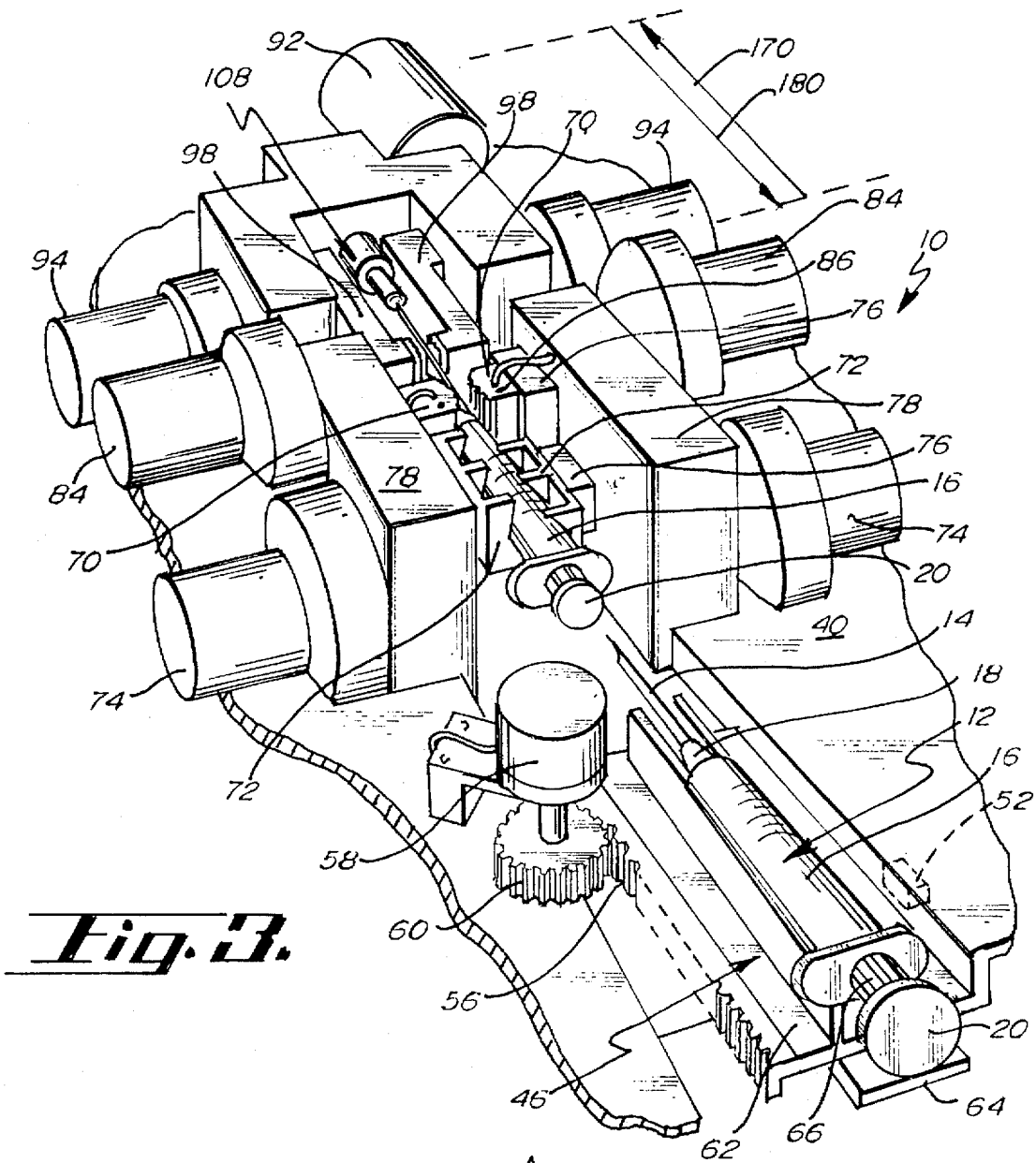
FIG. 3 is an isometric view of the hypodermic needle extraction disposal device with the housing removed and the base platform shown in broken sections.

Simultaneously to the heating of the lure 18 by the cartridge heater assembly, the needle extraction assembly engages the needle The needle extraction platform 90 may include a positioning member 106 which is adapted for engagement to the needle extraction assembly channel 50 providing for the linear motion of the needle extraction platform 90 with respect to the inclined base platform 40 as indicated by arrows 170 and 180 of FIG. 3. It should be noted that the forward positioning 180 of the needle extraction platform 90 may be limited by the length of the needle extraction assembly channel 50 or through the electronic control system 150 via the programming of an exact distance for forward rotation of the needle extraction shaft 102. It should also be noted that the inward or forward positioning 180 of the needle extraction platform 90 is a known distance which may be preprogrammed as a threshold within the microprocessor 118.

The at-rest position for the needle extraction assembly is adjacent to the cartridge heater assembly. In order to engage the needle 14, the electronic control system 150 signals the needle tip clamp motors 94 to rotate the screw shafts 82 for inward positioning of the square plungers 76 within the square plunger channels 80 as engaged to the needle extraction motor mount blocks 96. The needle tip gripper jaws 98, having the knurled carbide grippers 100, may be affixed to the square plungers 76 via the recessed adaptor front surface as earlier described. It should be noted that the operations, interaction, and advantages as earlier described for the square plungers 76, motor mount blocks 78, square plunger channels 80, screw shafts 82, and nut certs as earlier described, are equally applicable to the needle extraction assembly. The needle tip clamp motors 94 continue to apply power for the grasping of the needle 14 by the needle tip gripper jaws 98. As the pressure increases between the needle tip gripper jaws 98 and the needle 14, a signal is communicated to the electronic control system 150 for an increased level of voltage or current to be utilized by the needle tip clamp motors 94. The electronic control system 150 then signals the needle tip clamp motors 94 to terminate further inward rotation of the screw shafts 82 which maintains a secure clamping of the needle 14 between the needle tip gripper jaws 98. Simultaneously with the signal from the electronic control system 150 to terminate further pressure to be exerted upon the needle 14 by the needle tip gripper jaws 98, the electronic control system 150 signals the needle extraction motor 92 to exert a retracting pressure upon the needle extraction platform 90.

The needle extraction motor 92 then moves the needle extraction platform 90 rearwardly 170 away from the lure 18. The needle extraction platform 90 is moved rearwardly 170 via the rotational engagement of the needle extraction shaft 102 as engaged to a threaded nut 104, which may be affixed to, or integral with, the needle extraction platform 90.

As the lure 18 becomes softened following exposure to heat from the heat heads 70, the engagement between the needle 14 and the lure 18 becomes weaker. At some point, the lure 18 has become sufficiently soft to permit the extraction of the needle 14 from the lure 18. During this entire sequence, the needle extraction motor 92 is exerting a retraction pressure upon the needle extraction platform 90. The needle extraction motor 92, during this operation, waits for a reduction in the current requirement for extraction of the needle 14, which is indicative of the softening of the lure 18 and the release of the needle 14 from the lure 18. The electronic control system 150 is then able to sense the imminent extraction of the needle 14 from the syringe 12 as pulled from the softened lure 18, whereupon, the electronic control system 150 provides an instruction to the needle extraction motor 92 to increase power to further retract the needle tip gripper jaws 98 rearwardly 170 for separation of the needle 14 from the lure 18. It should be noted that the extracting pressure exerted by the needle extraction motor 92 is not excessive but does provide a small constant tugging force upon the needle 14 with respect to the syringe 12. The level of force exerted by the needle extraction motor 92 is sufficient to sense the softening of the lure 18 and the slippage and retraction of the needle 14 from the. The electronic control system 150 then continues to signal the needle extraction motor 92 to retract the needle extraction platform 90 outwardly 170 away from the cartridge heater assembly through an increased level of current, voltage, and/or power. It should be noted that the needle 14 inside the lure 18 may be three quarters of an inch in length for large blood draw syringes 12. The outward retraction of the needle extraction platform 90 from the cartridge heater assembly then separates the needle 14 from the lure 18.

It should be noted that the needle tip clamp motors 94 and needle tip gripper jaws 98 are adapted for grasping of any diameter of needle 14 which may range between twenty-eight gauge thickness to the larger sixteen gauge thickness needles. It should also be noted that the extraction of a needle 14 from a syringe 12 and the interaction between the barrel clamp assembly, cartridge heater assembly, and needle extraction assembly is based upon an event system as opposed to a timing sequence. Therefore, the interrelationship between the barrel clamp assembly, cartridge heater assembly, and/or needle extraction assemblies are not affected by the diameter dimensions for the syringe body 16 or the needle 14. It should again be noted that the electronic control system 150 operates the needle extraction motor 92 and/or the needle tip clamp motors 94 based upon the analysis of the voltage/current requirements for exertion of a desired amount of pressure whereupon the electronic control system 150 will signal the respective needle extraction motor 92 or needle tip clamp motors 94 to hold an acquired position.

Figure 6:
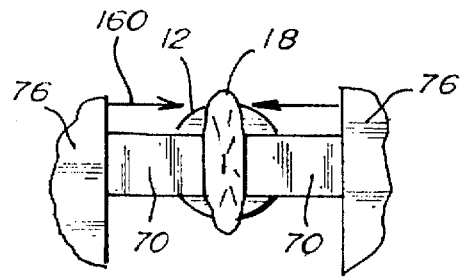
FIG. 6 is a front detailed view of the cartridge heaters engaged to the lure of a syringe.
Figure 7:
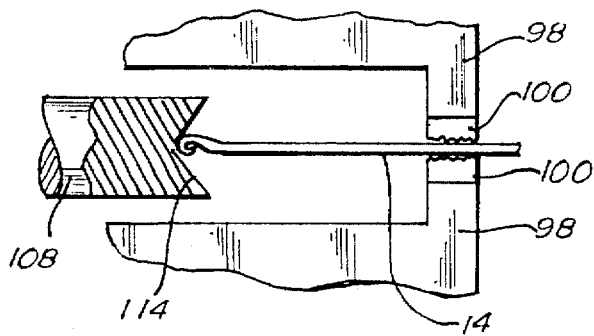
FIG. 7 is a detailed broken away side view of the needle tip contactor, needle, and needle tip gripper jaw heads during the blunting and sterilization of the needle.

Simultaneously with the needle 14 separating from the lure 18, the electronic control system 150 signals the ferrule clamp motors 84 to engage to pinch and collapse 160 the softened lure 18 by the heat heads 70 for sealing of the internal cavity of the syringe body 16. (FIGS. 5 and 6) It should be noted that the inclined base platform 40 facilitates the prevention of biological substances to escape the syringe body 16 due to the upward positioning of the lure 18 with respect to the syringe body 16. The ferrule clamp motors 84 continue to exert compression pressure upon the lure 18 until such time as a threshold is reached whereon the electronic control system 150 signals the ferrule clamp motors 84 to retract to an at-rest or re-start position.

Simultaneously with the compression and sealing of the 84, lure 18 by the heat heads 70, via the ferrule clamp motors the needle extraction assembly is further retracted rearwardly 170 for engagement of the needle 14 to the needle tip contactor assembly.

It is important to note that the positioning of the needle tip gripper jaws 98 proximate to the lure 18 facilitates the sterilization of the needle 14 by the needle tip contactor by maximizing the distance between the end or tip of the needle 14 and the contact location for the carbide grippers 100 which form an electrical contact when the needle is engaged to the tip contactor 108.

Immediately following the sealing of the syringe cavity, the heat heads 70 are retracted to their at-rest start position and the electrical control system 150 signals the barrel clamp motors 74 to retract the barrel clamp heads 72 to their retracted start position which permits the syringe body 16 to drop through the syringe body aperture 44 into the syringe body bin 30.

It is important to note that the compression and sealing of the lure 18 by the heated heads 70 occurs virtually immediately upon the extraction of the needle 14 from the plastic lure 18 as the base of the needle 14 clears the tip of the plastic lure 18. Immediate compression of the lure 18 upon the separation of the needle 14 from the syringe lure 18 ensures that no contamination or contaminated substance escapes from the syringe 12.

Following the separation of the needle 14 from the lure 18, the needle 14 is sterilized through the establishment of an electrical contact and subsequent heating with the needle tip contactor 108. The needle tip contactor 108 is preferably engaged to an inverted L-bracket 110 and to a spring 112. The tip contactor 108 preferably includes a conical shaped receiving end 114 which is adapted to engage the tip of a needle 14. The tip contactor 108 is preferably in electrical communication with the carbide grippers 100 of the needle tip gripper jaws 98. The inverted L-bracket 110 is preferably fixedly positioned with respect to the inclined base platform 40 at a sufficient distance to permit the retraction of the needle extraction platform 90 rearwardly 170 from the cartridge heater assembly.

The tip contactor 108 is preferably spring loaded via a spring 112 and may be formed of a one quarter inch brass diameter shaft having a conical shaped receiving end 114. A needle 14 engaging the receiving end 114 may thereby be centered for sterilization and processing. Upon engagement of the needle 14 with the tip contactor 108, an electrical connection is established whereon the electronic control system 150 applies power across the needle 14 whereupon the needle 14 is used as an element. The electronic control system 150 preferably places approximately twelve to twenty volts corresponding to twelve to fifteen amps across the needle 14 which instantaneously sterilizes any chemistry or blood which may be present upon the needle 14. The needle temperature is then raised to approximately 1100° fahrenheit. Simultaneously, the conical shaped receiving end 114 upon the heating of the needle 14 deforms the point blunting the end of the needle 14 into a non-reusable condition. It is important to note that the needle tip grippers jaws 98 grasp the needle 14 proximate to the lure 18 in order to maximize the distance between the tip of the needle 14 and the carbide grippers 100. The maximum amount of heating of the needle 14 is thereby provided ensuring that the portion of the needle 14 as extracted from the lure 18 receives an appropriate amount of energy for sterilization.

The electronic control system 150 then terminates the application of energy across the needle 14 whereupon the needle extraction motor 92 actuates the needle extraction platform 90 forwardly 180 for return to the at-rest position. The needle 14 is thereby separated from the conical receiving end 114. The electronic control system 150 then signals the needle tip clamp motors 94 to retract, separating the needle tip gripper jaws 98 from the needle 14 permitting the needle 14 to drop through the needle aperture 42 for storage within the needle bin 28. All the elements of the hypodermic needle extraction and disposal device 10 are then positioned for processing of another used syringe 12.

Figure 8:
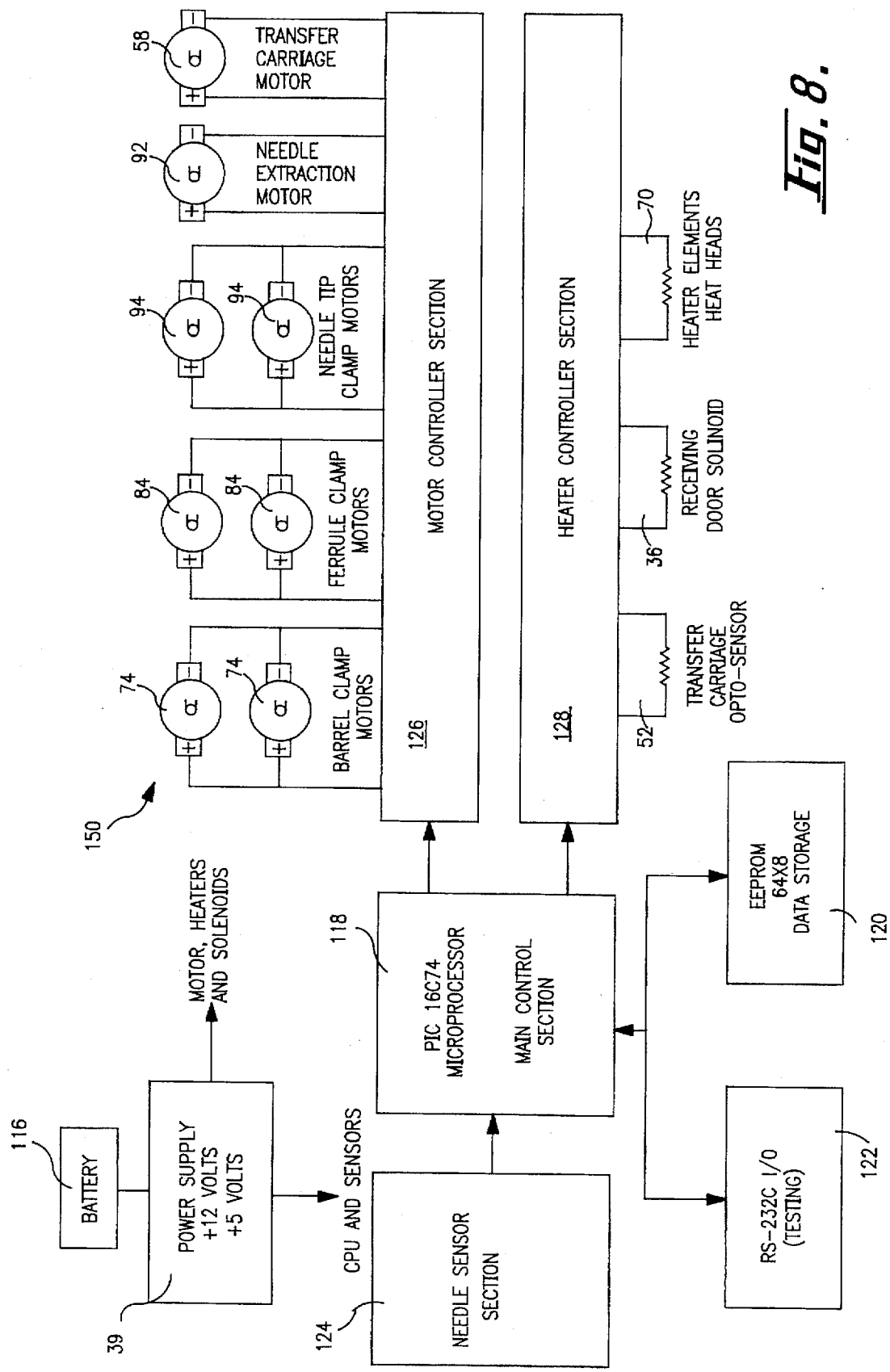
FIG. 8 is a generalized block diagram of the circuitry for the hypodermic needle extraction disposal device.
Figure 9:
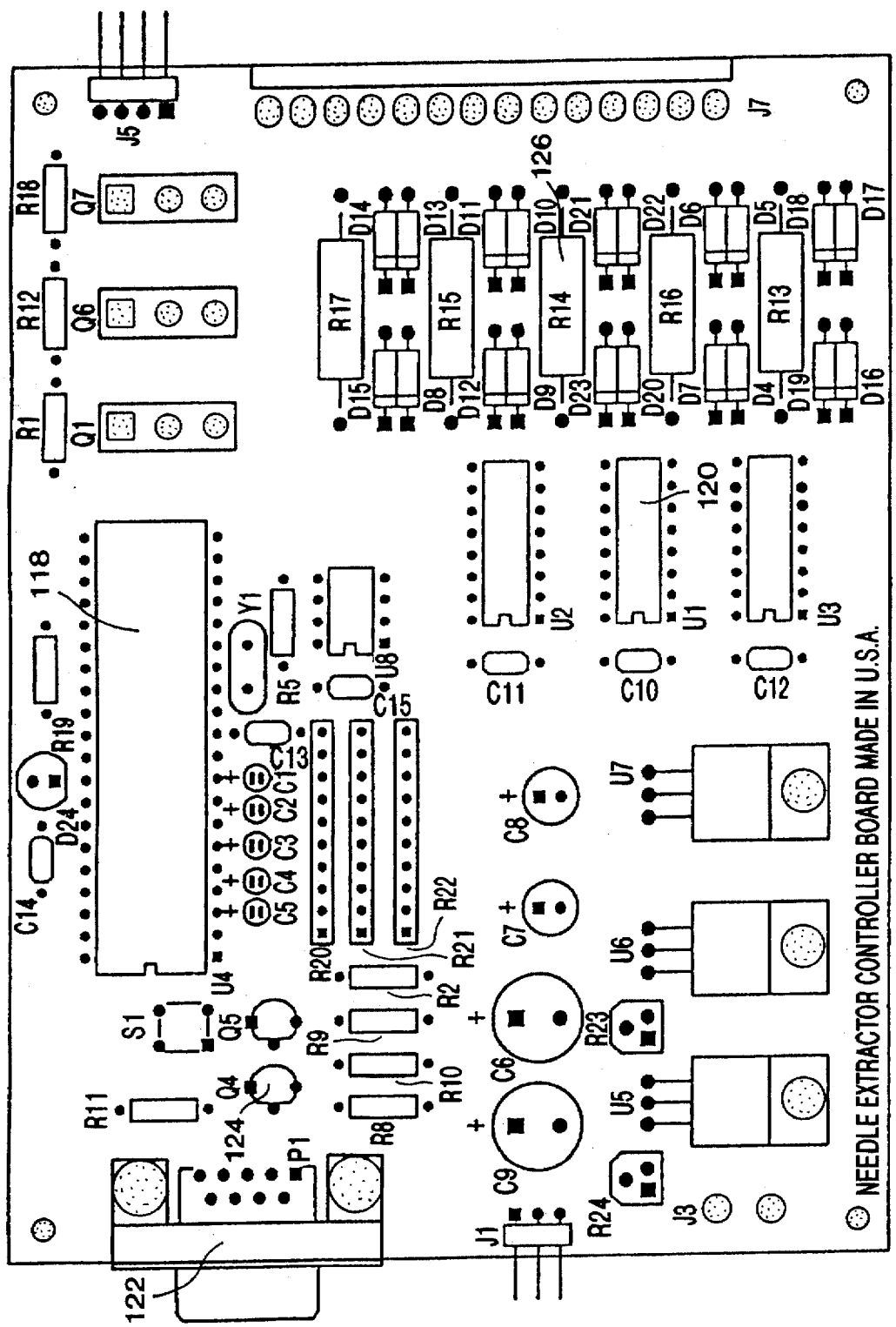
FIG. 9 is a circuit board lay-out of the top side of the circuit board.
Figure 10:
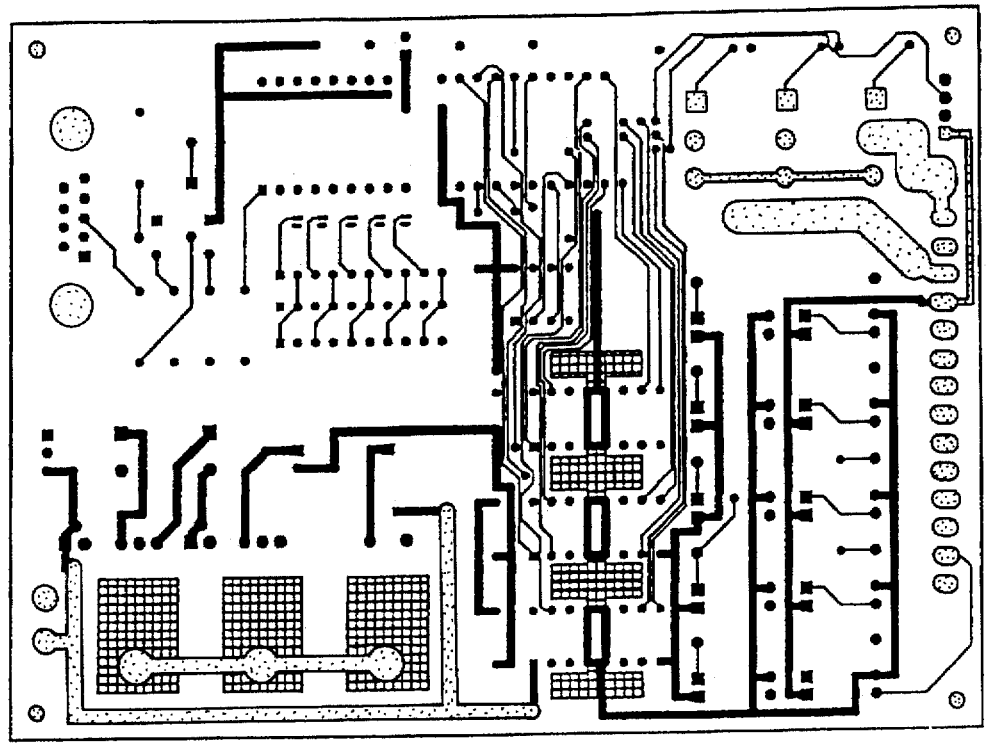
FIG. 10 is the component side of the circuit board layout for the circuit board.
Figure 11:
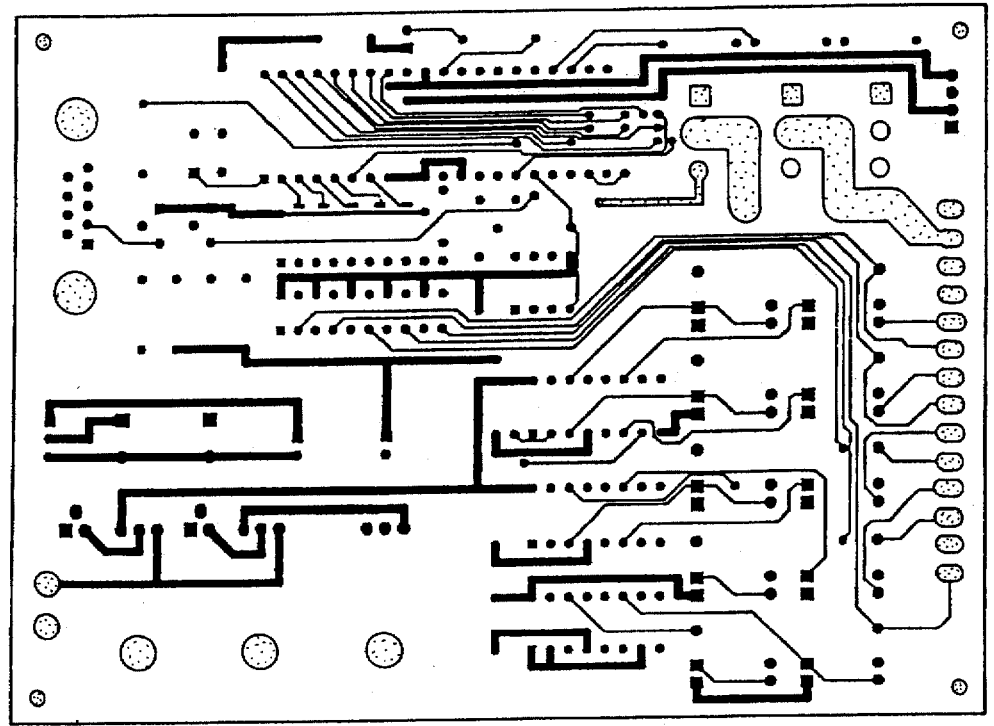
FIG. 11 is the solder side of the circuit board lay-out for the circuit board.
Figure 12A:
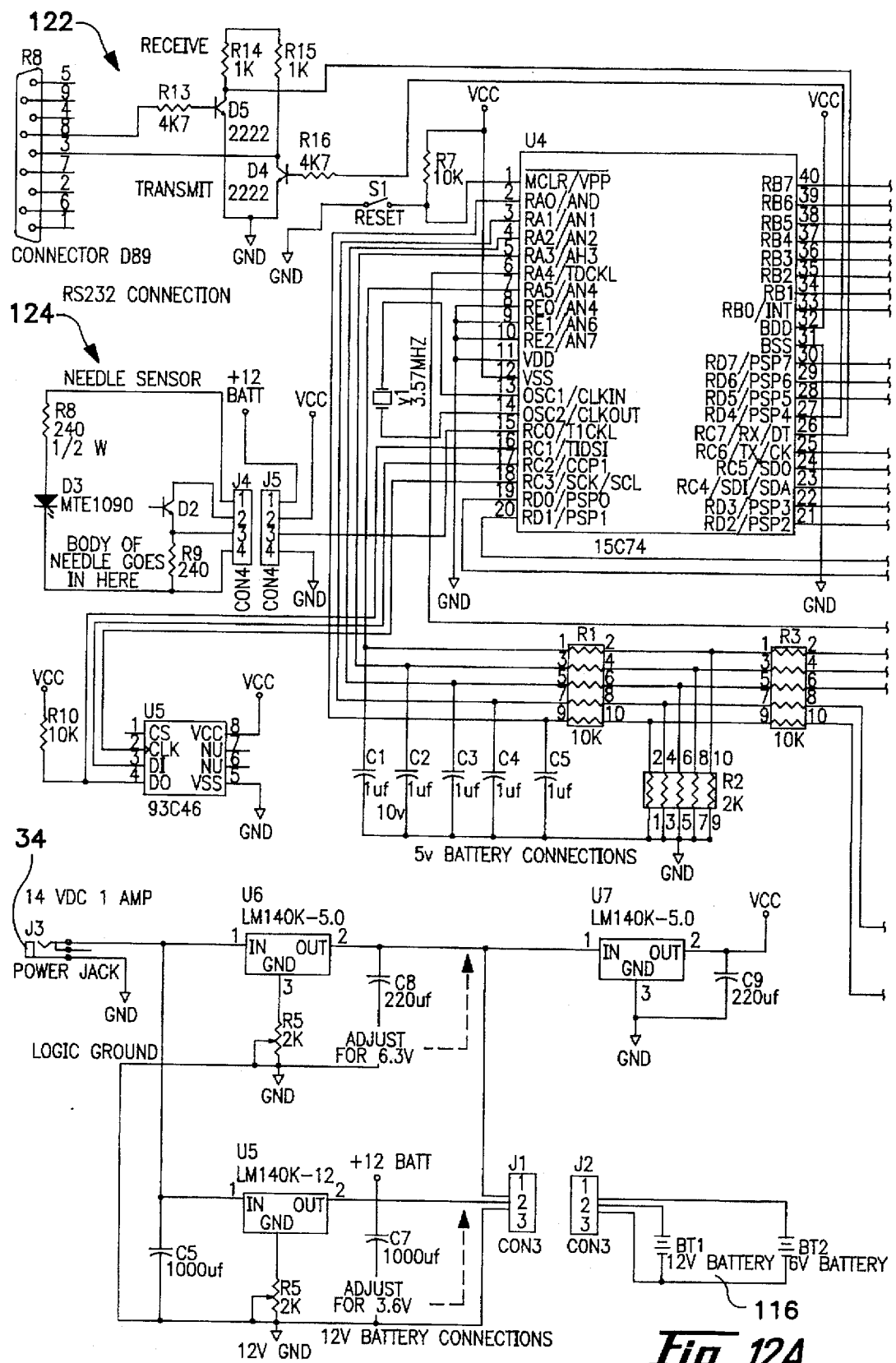
FIGS. 12a, 12b, and 12c are detailed circuit schematics of the hypodermic needle extraction disposal device.
Figure 12B:
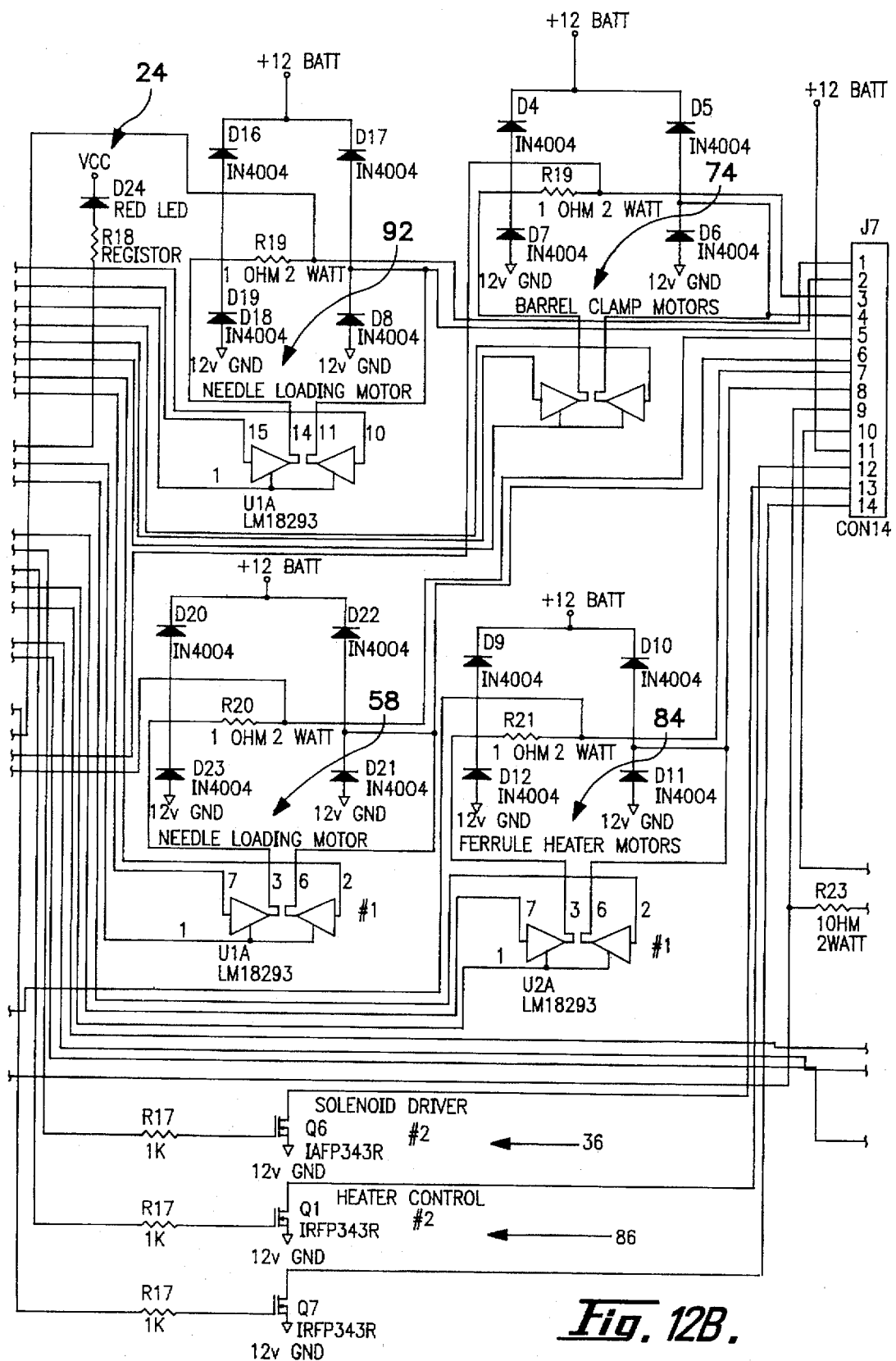
Figure 12C:
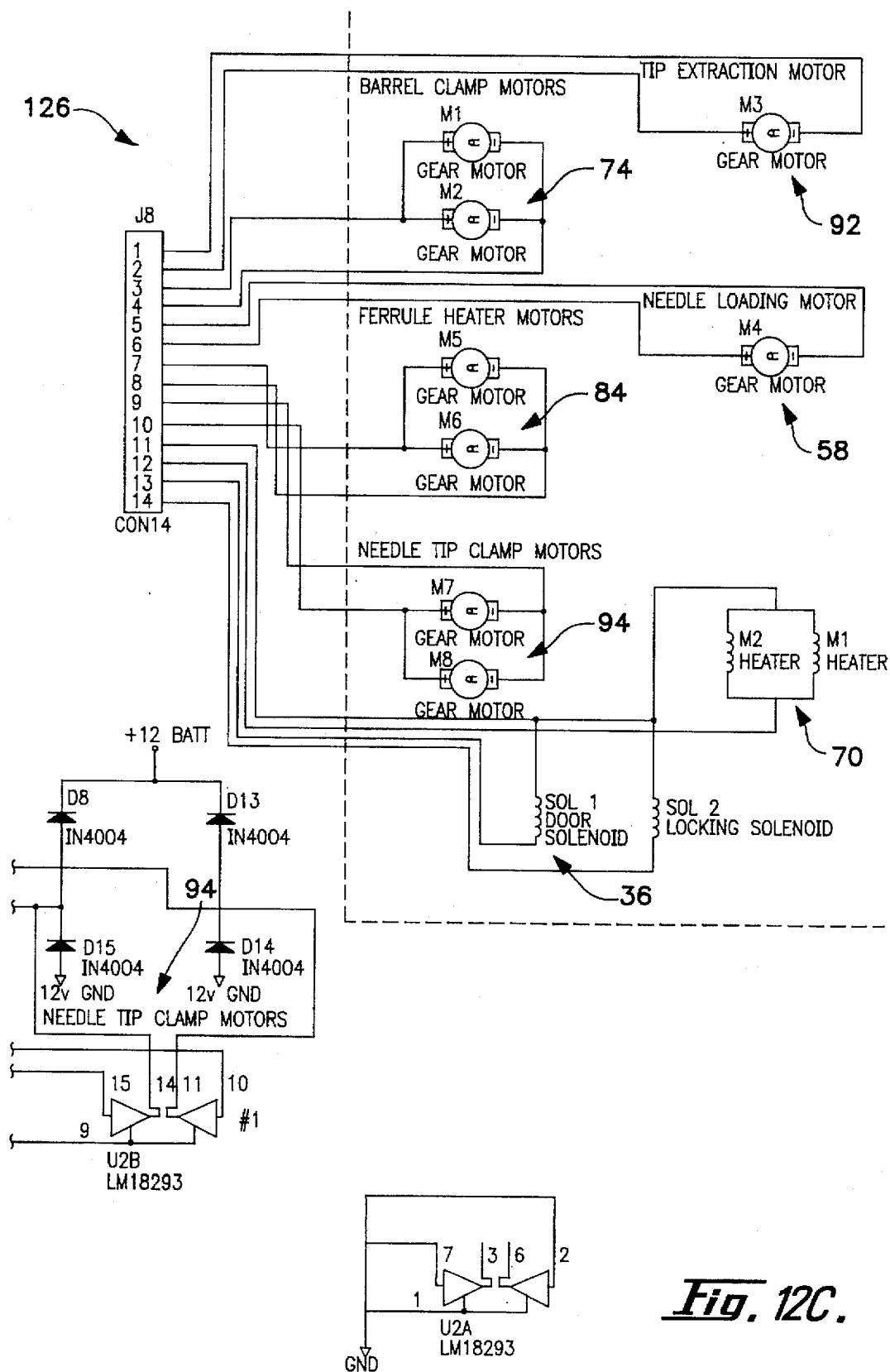
Figure 13A:
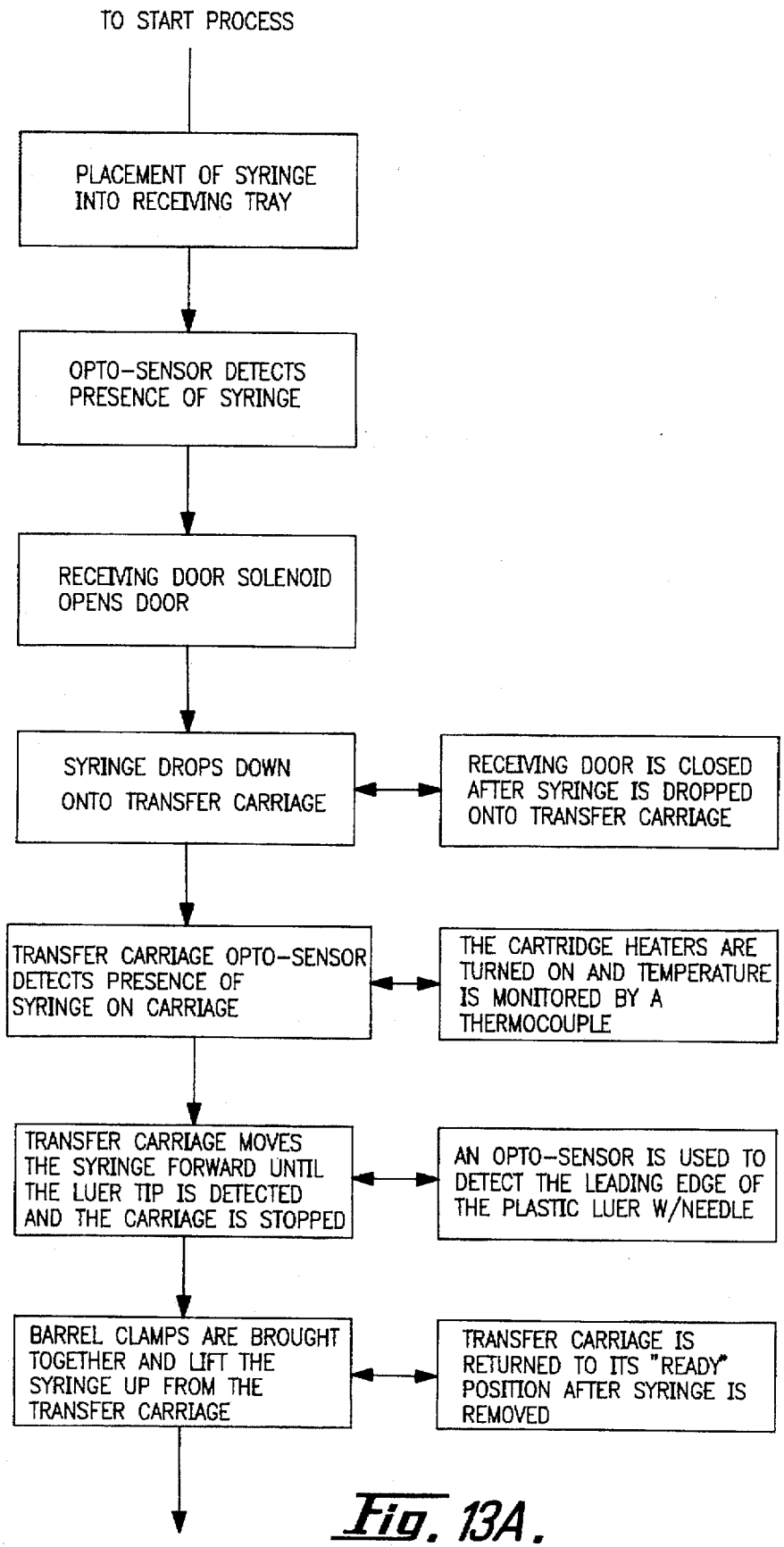
FIG. 13a, 13b, and 13c represent a flow chart of the program and method of process for the transfer, sterilization, and disposal procedures for the hypodermic needle extraction disposal device.
Figure 13B:
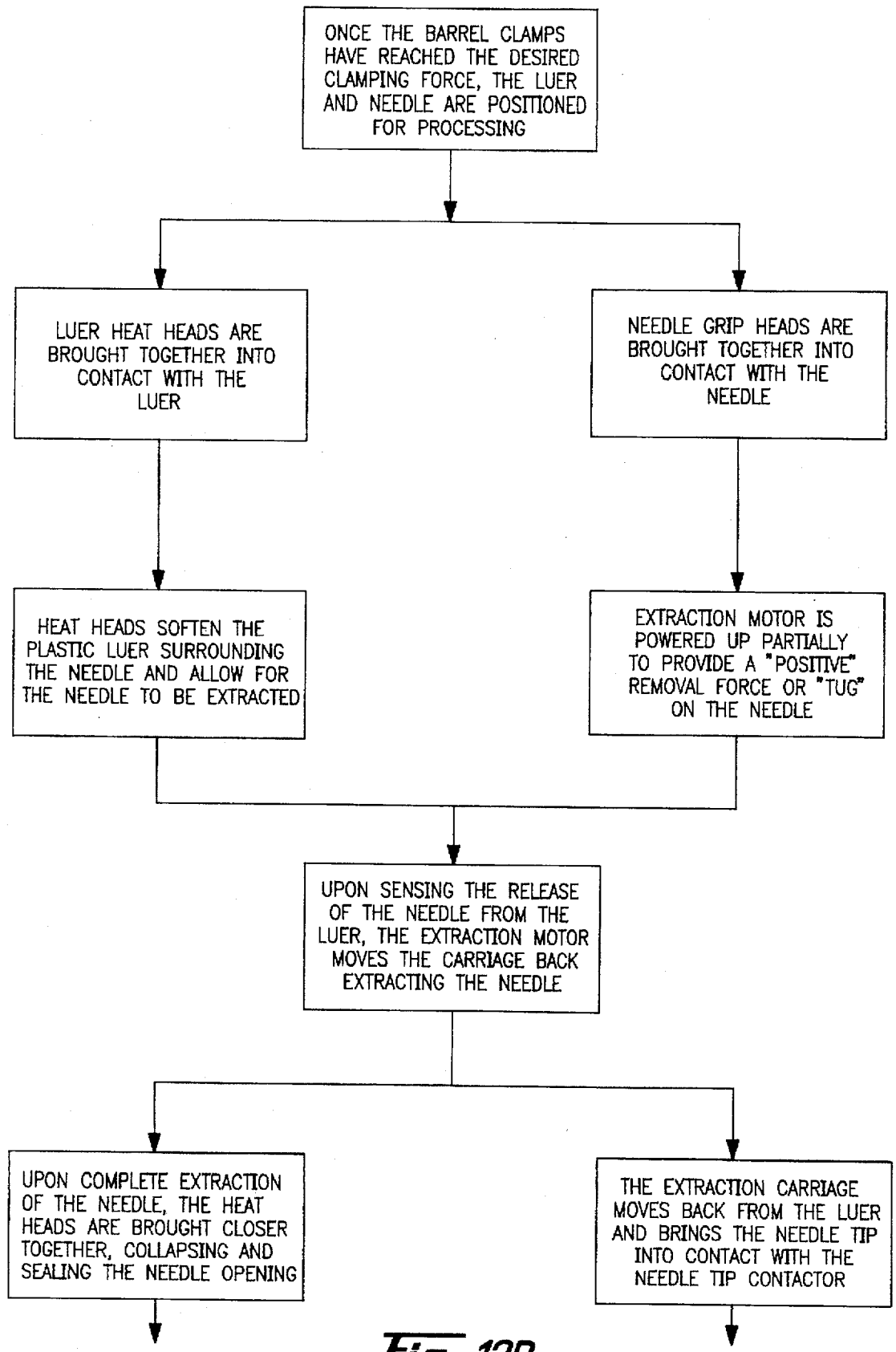
Figure 13C:
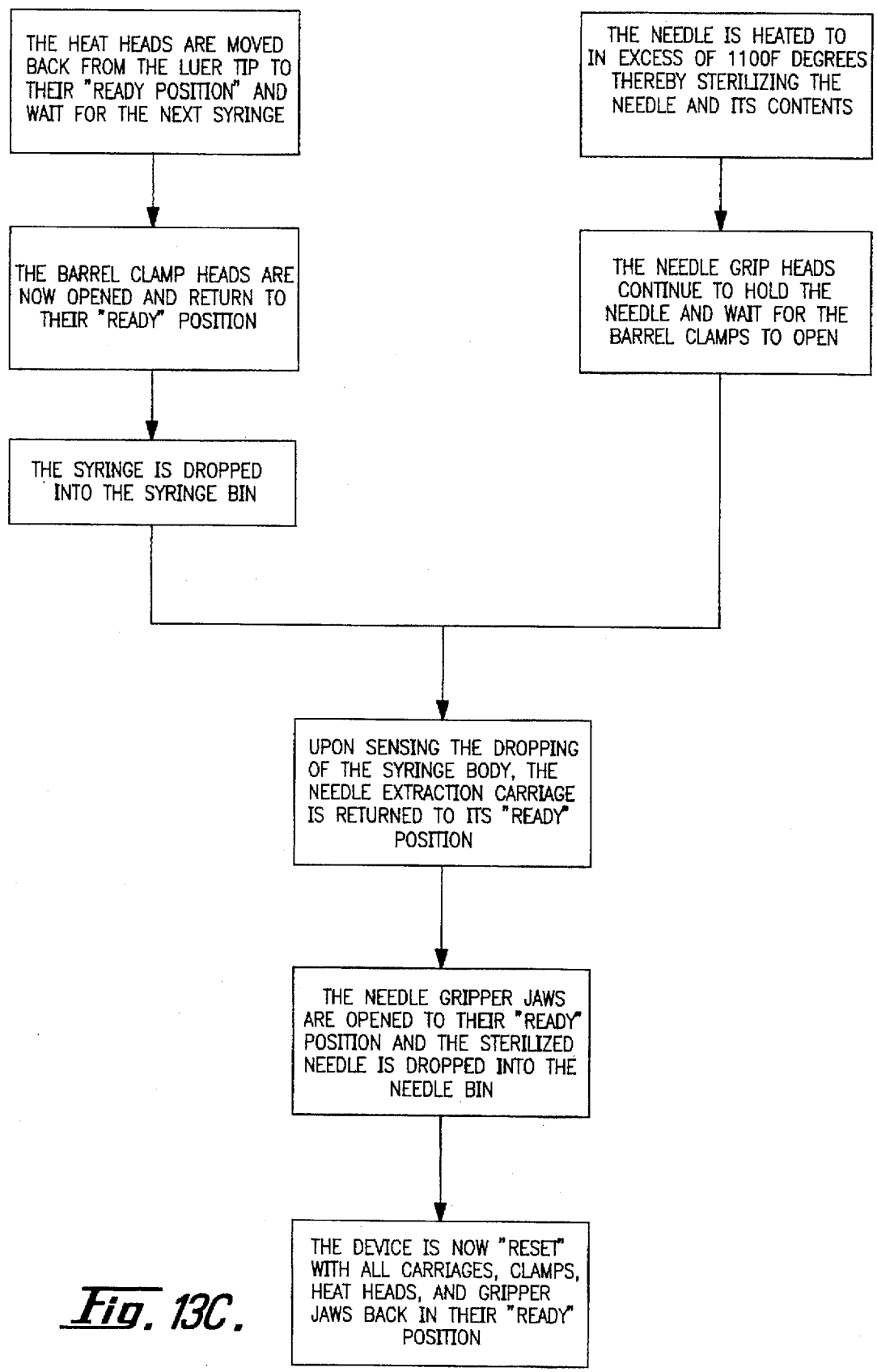

A block diagram representing the electronic control system 150 is depicted in FIG. 8. A rechargeable battery 116 is preferably electrically connected to the power supply 39. The battery 116 may be charged or recharged by either a standard electrical wall outlet fixture through the power input jack or through connection to a cigarette lighter of a motor vehicle providing twelve volts of power to the power input jack. The battery 116 and/or the power supply 39 preferably provide power to the microprocessor 118.

The microprocessor 118 is preferably in electrical communication with the memory or EPROM 120 which preferably stores the instruction codes, thresholds, and operational parameters for the hypodermic needle extraction disposal device 10. The microprocessor 118 is also preferably in communication with the RS232 port 122 of the circuit board. The RS232 port 122 permits communication with the memory for adjustment of the timing and/or the sensing sequence threshold levels for the operation of the hypodermic needle extraction disposal device 10.

The microprocessor 118 is also preferably in communication with a needle sensor section 124. The needle sensor section 124 signals the microprocessor 118 to communicate with the motor controller section 126 for engagement or regulation of the barrel clamp motors 74 during the lifting of the syringe 12 from the transfer carriage 46. In addition, the needle sensor section 124, through the transfer carriage stop opto-sensor 68, signals the microprocessor 118 of the position of the syringe 12 where the microprocessor 118 then communicates with the motor controller section 126 for initiation of the engagement of the ferrule clamp motors 84 and the needle tip clamp motors 94 for heating of the lure 18 and clamping of the needle 14 by the needle tip gripper jaws 98.

The needle sensor section 124 is also sensing the voltage current requirements of the needle extraction motor 92 and communicates to the microprocessor 118 an experienced voltage or current drop which signals the release of the needle 14 from the lure 18. The needle sensor section 124 then signals the microprocessor 118 which in turn communicates with the motor controller section 126 to add power to the needle extraction motor 92 to separate the needle 14 from the lure 18.

The needle sensor section 124 also senses the engagement of the needle 14 with the tip contactor 108 providing a signal to the microprocessor 118 which in turn communicates with the heater controller section 128 to place a current across the needle 14 to effect sterilization.

The needle sensor section 124, through the receiving door opto-sensor 38, signals the microprocessor 118 of the existence of a syringe 12 available for processing which, in turn, initiates a signal from the microprocessor 118 to the heater controller section 128 to activate the syringe receiving door 36 for placement of a syringe 12 upon the transfer carriage 46. The needle sensor section 124, through the transfer carriage stop opto-sensor 68, also senses the positioning of a syringe 12 adjacent to the heat heads 70 which then signals the microprocessor 118 which, in turn, initiates communications with the motor controller section 126 for activation of the ferrule clamp motors 84 and simultaneously communicates with the heater controller section 128 for activation of the heat heads 70.

The motor controller section 126 receives signals from the microprocessor 118 for regulation of the current/voltage to be available for positioning of the barrel clamp motors 74, the ferrule clamp motors 84, the needle tip clamp motors the needle extraction motor 92, and the transfer carriage motor 52. The motor control section 126 further regulates the pressure to be exerted during the clamping of the syringe body 16, the needle 14, and the sealing of the lure 18. The motor controller section 126 also controls the transfer carriage assembly and the barrel clamp assembly of the hypodermic needle extraction and disposal device 10. The pressure thresholds and/or voltage/current thresholds utilized to control the transfer carriage assembly, barrel clamp assembly, cartridge heater assembly, needle extraction assembly, and the needle tip contactor are available to the microprocessor 118 from the memory 120.

It should be noted that the memory 120, and the microprocessor 118 in communication with the needle sensor section 124, operate on an event-based system and not as a timing system or sequence for the control of the motor controller section 126 and the heater controller section 128.

Specifically, the microprocessor 118, memory 120, and needle sensor section 124, communicate signals to a specific motor of the motor controller section 126 until a certain event has occurred, at which time a new command is issued for the next procedural operation.

Also, the microprocessor 118, memory 120, and needle sensor section 124 communicate signals to the heater controller section 128 to engage the heat heads 70 to elevate the temperature of the heat heads 70 to a specific temperature as monitored by the thermalcouples 86, and to regulate the temperature of the heat heads 70 to remain within a specified preprogrammed level.

The microprocessor 118 also functions to determine and analyze current or voltage drops or demands for comparison to the memory 120 to determine a required action.

It should also be noted that the microprocessor 118 performs continuous and repetitive parallel processing analysis for regulating and controlling a number of functions of the hypodermic needle extraction and disposal device 10 simultaneously as an event-based system.

The parallel processing of the microprocessor 118 enhances the flexibility of the hypodermic needle extraction and disposal device 10 for processing of syringes 12 having varying lengths and diameters. As such, the microprocessor 118 waits to receive signals from the needle sensor section 124 that certain actions have occurred. The microprocessor 118 is programmed to not initiate certain actions until a signal is received that a predecessor action has been completed. The time required to complete an individual action is not of consequence to the microprocessor 118 because the timing of certain actions may vary dependent upon the size dimensions of a syringe 12 to be processed.

The flexibility of the microprocessor 118 and the hypodermic needle extraction and disposal device 10 eliminates the necessity for changing grippers or barrel clamps for processing of different sized syringes 12. The microprocessor 118, in communication with the transfer carriage assembly, and barrel clamp assembly, positions a needle 14 in an exact x-y coordinate or plane for sterilization processing by the cartridge heater assembly, needle extraction assembly, and the needle tip contactor 108.

The present invention may be embodied in other specific forms without departing from the spirit or essential attributes thereof, therefore, the illustrated embodiment should be considered in all respects as illustrative and not restrictive, reference being made to the appended claims rather than to the foregoing description to indicate the scope of the invention.

What is claimed:

1. A hypodermic needle extraction device comprising:
   (a) a transfer carriage assembly for carrying a syringe said transfer carriage assembly comprising a gear rack, a transfer carriage motor having a gear engaged to said gear rack for providing motion to said transfer carriage;
   (b) a barrel clamp assembly for grasping said syring;
   (c) a cartridge heater assembly for heating said syringe;
   (d) a needle extraction assembly adjacent to said cartridge heater assembly for grasping a needle of said syringe and separating said needle from said syringe; and
   (e) a needle tip contactor adjacent to said needle extraction assembly, said needle tip contactor comprising a means for heating of said needle.

2. The hypodermic needle extraction device of claim 1, further comprising a means for stopping to limit said motion of said transfer carriage.

3. The hypodermic needle extraction device of claim 1, said barrel clamp assembly further comprising a pair of barrel clamp motors and a barrel clamp head engaged to each of said barrel clamp motors, said barrel clamp motors for providing motion to said barrel clamp heads for grasping of said syringe between said barrel clamp heads.

4. The hypodermic needle extraction device of claim 3, said cartridge heater assembly comprising a pair of ferrule clamp motors and a cartridge heater engaged to each of said ferrule clamp motors for heating of said syringe.

5. The hypodermic needle extraction device of claim 4, said needle extraction assembly comprising a needle extraction platform having a needle extraction platform motor, a pair of needle tip clamp motors, each of said needle tip clamp motors having a needle tip gripper jaw for gripping of said needle.

6. The hypodermic needle extraction device of claim 5, further comprising a housing having a needle bin and a syringe bin for storage of said needles and said syringes having said needles removed therefrom.

7. The hypodermic needle extraction device of claim 5, further comprising an electronic control system comprising a power supply, a micro-processor, a memory, a needle sensor section, a sequence sensing section, a motor control section, and a heater control section for control and operation of said transfer carriage assembly, said barrel clamp assembly, said cartridge heater assembly, said needle extraction assembly, and said needle tip contactor.

8. A hypodermic needle extraction device comprising:
   (a) a transfer carriage assembly comprising a transfer carriage having a gear rack, a transfer carriage motor having a gear engaged to said gear rack for providing motion to said transfer carriage, and a means for stopping to limit said motion of said transfer carriage;
   (b) a barrel clamp assembly connected to said transfer carriage assembly, said barrel clamp assembly comprising a pair of barrel clamp motors and a barrel clamp head engaged to each of said barrel clamp motors, said barrel clamp motors for providing motion to said barrel clamp heads for grasping a syringe;
   (c) a cartridge heater assembly connected to said barrel clamp assembly, said cartridge heater assembly comprising a pair of ferrule clamp motors and a cartridge heater engaged to each of said ferrule clamp motors for heating of said syringe;
   (d) a needle extraction assembly adjacent to said cartridge heater assembly, said needle extraction assembly comprising a needle extraction platform motor, a pair of needle tip clamp motors, each of said needle tip clamp motors having a needle tip gripper jaw for grasping of a needle of said syringe; and
   (e) a needle tip contactor adjacent to said needle extraction assembly, said needle tip contactor comprising a means for heating of said needle.

9. A method of process for extraction of a needle from a syringe, said method comprising:
   (a) placing a syringe having a needle and a front onto a transfer carriage assembly;
   (b) moving said transfer carriage assembly to a position adjacent to a barrel clamp assembly, said barrel clamp assembly having barrel clamp heads;
   (c) grasping said syringe by said barrel clamp heads;
   (d) positioning of a cartridge heater assembly adjacent to said syringe;
   (e) clamping said needle by a needle extraction assembly;
   (f) heating said syringe adjacent to said needle;
   (g) retracting said needle extraction assembly separating said needle from said syringe;
   (h) pinching said syringe proximate to said front;
   (i) engaging said needle to a needle tip contactor; and
   (j) heating said needle.

10. The method of process of claim 9, said moving said transfer carriage assembly further comprising engaging a transfer carriage motor having a transfer carriage gear for moving said transfer carriage assembly.

11. The method of process of claim 10, said grasping said syringe comprising engaging a pair of barrel clamp motors, each barrel clamp motor having a barrel clamp head for grasping, elevating, and positioning of said syringe in a desired x-y plane.

12. The method of process of claim 11, said positioning of a cartridge heater assembly adjacent to said syringe comprising engaging a pair of ferrule clamp motors, each of said ferrule clamp motors having a cartridge heater for positioning adjacent to said front of said syringe.

13. The method of process of claim 12, said clamping said needle by a needle extraction assembly comprising engaging a needle extraction platform motor for moving said needle extraction assembly proximate to said cartridge heater assembly.

14. The method of process of claim 13, further comprising engaging a pair of needle tip clamp motors, each of said needle tip clamp motors having a needle tip grasping jaw grasping said needle.

15. The method of process of claim 14, said heating said syringe comprising applying power to said cartridge heaters for heating said front of said syringe.

16. The method of process of claim 15, said pinching said syringe comprising manipulating said cartridge heaters into engagement with said front of said syringe and pinching said front of said syringe into a sealed configuration.

17. A hypodermic needle extraction device comprising:
   (a) a transfer carriage assembly for carrying a syringe;
   (b) a barrel clamp assembly adjacent to said transfer carriage assembly for grasping, lifting, and centering said syringe;

(c) a cartridge heater assembly adjacent to said barrel clamp assembly for heating said syringe;

(d) a needle extraction assembly adjacent to said cartridge heater assembly for grasping a needle of said syringe and separating said needle from said syringe; and (e) a needle tip contactor adjacent to said needle extraction assembly, said needle tip contactor comprising a means for heating of said needle.

* * * * *